US008917923B2

(12) United States Patent
Grosskopf et al.

(10) Patent No.: US 8,917,923 B2
(45) Date of Patent: Dec. 23, 2014

(54) METHOD AND CT SYSTEM FOR RECORDING AND DISTRIBUTING WHOLE-BODY CT DATA OF A POLYTRAUMATIZED PATIENT

(75) Inventors: Stefan Grosskopf, Nürnberg (DE); Daniel Ruzicka, Nürnberg (DE); Michael Scheuering, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 209 days.

(21) Appl. No.: 13/547,367

(22) Filed: Jul. 12, 2012

(65) Prior Publication Data

US 2013/0022256 A1 Jan. 24, 2013

(30) Foreign Application Priority Data

Jul. 15, 2011 (DE) .......................... 10 2011 079 270

(51) Int. Cl.
*G06K 9/00* (2006.01)
*A61B 6/00* (2006.01)
*A61B 6/03* (2006.01)

(52) U.S. Cl.
CPC ................. *A61B 6/563* (2013.01); *A61B 6/032* (2013.01); *A61B 6/5294* (2013.01)
USPC ....................................................... 382/131

(58) Field of Classification Search
None
See application file for complete search history.

(56) References Cited

U.S. PATENT DOCUMENTS

| 2002/0181646 A1* | 12/2002 | Mehldau ............................ 378/8 |
| 2004/0013293 A1* | 1/2004 | Klingenbeck-Regn ....... 382/131 |
| 2004/0068197 A1 | 4/2004 | Sarel |
| 2008/0267471 A1* | 10/2008 | Yu et al. ........................ 382/128 |
| 2009/0016584 A1* | 1/2009 | Boeing et al. ................ 382/128 |
| 2009/0226065 A1* | 9/2009 | Chen ............................ 382/131 |

FOREIGN PATENT DOCUMENTS

| DE | 10126641 A1 | 12/2002 |
| DE | 102007032302 A1 | 1/2009 |
| WO | WO-2007-037848 A2 | 4/2007 |

OTHER PUBLICATIONS

Seifert, A. et al., "Hierarchical Parsing and Semantic Navigation of Full Body CT Data", Proceedings of SPIE. vol. 7259 (2009); Others; 2009.

Jahresbericht 2009 des Trauma Registers der DGU (Deutsche Gesellschaft für Unfallchirurgie) http://www.traumaregister.de/downloads/Jahresbericht_2009.pdf; Others.

(Continued)

*Primary Examiner* — Amara Abdi
(74) *Attorney, Agent, or Firm* — Harness, Dickey & Pierce, P.L.C.

(57) ABSTRACT

A method and CT system are disclosed for recording and distributing whole-body CT data of a polytraumatized patient. In at least one embodiment the method includes producing a whole-body topogram including division and assignment of z-coordinate regions of the whole-body topogram to different body regions; performing a whole-body CT scan with the recording of CT raw data; assigning the CT raw data to the different body regions; reconstructing CT image datasets on a computer of the CT system; and sending only body region-specific CT image datasets to a number of remote workstations operated by technical specialists.

17 Claims, 4 Drawing Sheets

(56) References Cited

OTHER PUBLICATIONS

P. Hilbert et al., "New aspects in the emergency room management of critically injured patients: A multi-slice CT-oriented care algorithm" Injury, Int J. Care Injured (2007), 38, pp. 552-558; Others.

Karl-Georg Kanz et al., "Research Trauma management incorporating focused assessment with computed tomography in trauma (FACTT)—potential effect on survival", Journal of Trauma Management & Outcomes 2010, 4;4; Others.

Xiang Sean Zhou et al., "Redundancy, redundancy, redundancy: the three keys to highly robust anatomical parsing in medical images", Proceedings of the international conference on Multimedia information retrieval (MRI 2010), pp. 175-184; Others.

German priority document application No. De 10 2011 079 270.8 filed Jul. 15, 2011 (not yet published).

German Office Action dated Feb. 10, 2012.

Chinese Office Action and Search Report issued in Chinese Application No. 201210243728.8, dated Mar. 10, 2014.

\* cited by examiner

METHOD AND CT SYSTEM FOR RECORDING AND DISTRIBUTING WHOLE-BODY CT DATA OF A POLYTRAUMATIZED PATIENT

PRIORITY STATEMENT

The present application hereby claims priority under 35 U.S.C. §119 to German patent application number DE 10 2011 079 270.8 filed Jul. 15, 2011, the entire contents of which are hereby incorporated herein by reference.

FIELD

At least one embodiment of the invention generally relates to a method and/or CT system for recording and distributing whole-body CT data of a polytraumatized patient using a CT system, with which, to perform a differential diagnosis, reconstructed CT image datasets are sent from the CT system to a number of remote workstations operated by technical specialists to determine a diagnosis.

BACKGROUND

It is generally known that in traumatology whole-body CT scans are used increasingly, in some instances as the first and only imaging operation, in the context of a trauma room algorithm to reduce overall imaging time as much as possible and to determine a reliable diagnosis at an early stage, thereby increasing the patient's chances of survival and rehabilitation.

One problem with this procedure is that supplying the data from the whole-body CT results in extremely long data transfer times due to the size of the datasets in relation to existing data transfer rates in a standard network, in which the individual workstations of the diagnosing experts are located. This largely eliminates the time advantage that results from performing a whole-body CT rather than a number of individual examinations.

SUMMARY

At least one embodiment of the invention is directed to an improved method for the more efficient transfer of CT data to specific workstations.

Advantageous developments of the invention are the subject matter of subordinate claims.

The inventors have identified the following:

If, in the context of a trauma room algorithm including the performance of a whole-body CT scan, the diagnosis in the region of different organs is to be distributed to different experts or time phases of the trauma room algorithm are to be distributed, the whole-body CT dataset can expediently be broken down into body regions or injured regions before being sent to different experts' workstations, in order to reduce the quantity of data that has to be transferred to each workstation. This also benefits algorithms for further processing the CT image data at the workstations, e.g. CAD algorithms for detecting pathologies, as smaller image datasets can be processed more successfully.

It is therefore not necessary to transfer the complete whole-body CT datasets by way of the hospital network to the diagnosis workstations after CT acquisition. Nor is it necessary for the experts at their workstations to find the relevant image regions within the complete whole-body CT datasets first. Until now in the prior art it was necessary to search the entire existing whole-body CT image dataset using automatic algorithms for this purpose. This also resulted in not insignificant delays in the workflow until now.

According to at least one embodiment of the present invention, before the data is sent, it is divided up into the body regions required for the respective diagnoses by the respective experts and only the reconstructed CT data is sent, which is of relevance for the examination in each instance. In some instances different reconstruction parameters can even be used during the reconstruction of the body regions, which are particularly favorable for the examination in question, based on the already known assignment of the predetermined body regions to specific diagnostic viewing. It is thus possible to reconstruct for example body regions, which are used to perform orthopedic diagnoses, using parameters which highlight bony structures particularly clearly, while body regions, which are sent to experts in the diagnosis of organs, e.g. spleen, liver, kidneys, etc., are reconstructed using parameters which allow soft part structures to be identified particularly clearly. If a multi-energy CT is also used, these requirements can also be applied correspondingly when using combination parameters for image combination or with multi-component breakdowns.

Generally one important advantage of at least one embodiment of this method is the fast availability of the smaller, broken-down datasets by way of a hospital network. The reduced size of the datasets means that they can also be viewed and processed more quickly. When breaking down the image data on the basis of topograms at the scanner it is possible to use specific parameterizations, e.g. specific head reconstruction kernels, for the respective body regions during the reconstruction of the CT raw data, thereby supplying improved image data generally for the respective examination.

In accordance with at least one embodiment of the basic concept described above, in at least one embodiment the inventors propose a method for recording and distributing whole-body CT data of an, in particular polytraumatized, patient using a CT system, said method having at least the following successive method steps:

producing a whole-body topogram including division and assignment of z-coordinate regions of the whole-body topogram to different body regions, performing a whole-body CT scan with the recording of CT raw data, assigning the CT raw data to the different body regions based on the determined z-coordinate regions, reconstructing CT image datasets on a computer of the CT system, representing the different body regions of the z-coordinate regions, and sending body region-specific CT image datasets in each instance to a number of remote workstations operated by technical specialists to determine a diagnosis in respect of the body region sent thereto.

In addition to the method described above with its different embodiments, the inventors also propose at least one embodiment of a CT system having a dedicated control and computation unit and a number of workstations in different medical specialist areas connected thereto in the manner of a network to form a diagnosis system, with computer programs for performing the method steps of one of at least one embodiment of the preceding method being stored in the control and computation unit and the workstations.

BRIEF DESCRIPTION OF THE DRAWINGS

The invention is described in more detail below with reference to example embodiments with the aid of the figures, in which only the features that are necessary for an understanding of the invention are shown. The following reference characters are used: 1: CT system; 2: first x-ray tube; 3: first detector; 4: second x-ray tube; 5: second detector; 6: gantry housing; 7: patient; 8: examination couch; 9: system axis; 10: control and computation unit; 11: contrast agent applicator; 12: EKG line; 13: memory; 14: computer program; 15.x: diagnostic workstations; 16: network; 17: topogram; 18: control and data line; 19: CT image data; A: division/assignment; D: detector raw data; Da-Dz: differential diagnosis; M: landmarks; P1-P4: reconstruction parameter sets; R1-Rn: reconstruction datasets; T: whole-body topogram; S: control commands; Sa-Sz: diagnosis-specific image datasets; S1-S5: method steps; I-VI: body regions.

In the figures.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In accordance with at least one embodiment of the basic concept described above, in at least one embodiment the inventors propose a method for recording and distributing whole-body CT data of an, in particular polytraumatized, patient using a CT system, said method having at least the following successive method steps:

producing a whole-body topogram including division and assignment of z-coordinate regions of the whole-body topogram to different body regions, performing a whole-body CT scan with the recording of CT raw data, assigning the CT raw data to the different body regions based on the determined z-coordinate regions, reconstructing CT image datasets on a computer of the CT system, representing the different body regions of the z-coordinate regions, and sending body region-specific CT image datasets in each instance to a number of remote workstations operated by technical specialists to determine a diagnosis in respect of the body region sent thereto.

It is naturally assumed in the description of at least one embodiment of this method that the z-coordinate region corresponds to the typical z-coordinates of the CT system used and the z-axis corresponds to the system axis, about which the gantry of the CT system rotates where there is no tilting.

As a result of the performance of this method only the CT data actually required for a specific diagnosis from a whole-body CT is transferred, thereby greatly reducing the quantity of data transferred and also avoiding the need for selecting data from all the CT data of a whole-body CT at the workstation.

With at least one embodiment of this inventive method each body region-specific CT image dataset can advantageously be reconstructed using individual reconstruction parameters. This allows optimum adaptation to the requirements of the specific diagnosis in each instance during the reconstruction—unlike the prior art in which all the scan data of a whole-body CT was reconstructed using the same reconstruction parameters.

It is also particularly advantageous if the body regions in the topogram are determined by means of automatic identification methods for typical body marks. In other words the limits of predefined body regions are identified automatically in that certain distinctive structures of the human body are automatically searched for and identified in the topogram, for example using pattern recognition methods, and then certain body regions are marked out, at least in respect of their z-positions, on the basis of their now known positions.

In principle in this process z-regions for body regions that overlap at least partially can also be marked out. In an extreme instance complete overlaps of predefined body regions can also occur. It is thus possible for example to define the body region of the spinal column, which runs from head to pelvis, with further body regions for lung or abdomen present therein. As described above, different reconstruction parameters can also be applied for these different body regions depending on the material to be assessed, for example bone or soft tissue. For example the same body region can even be reconstructed using two different reconstruction parameters depending on the tissue to be assessed, as is advantageous for the examination of the cranial bone on the one hand and the brain structure on the other hand. It is important that only the part of the reconstructed CT data that is relevant for the purpose is sent to the competent expert for the diagnosis in each instance.

To ensure the smoothest and fastest flow of data acquisition and data distribution possible, it is also advantageous, if an option for the manual correction of previously automatically identified body regions is provided in addition to the purely automatic identification of body features and determination of the desired body regions. With severely polytraumatized patients in particular it may be possible that some body features cannot be identified automatically because of the injury present, so that manual correction or manual inputting of the z-coordinate region for a desired body region is advantageous here.

It is also favorable if the different transferred CT datasets of the body regions are shown at the different workstations in different display modes tailored to the respective diagnosis. Thus for example different display variants for the CT data can be shown depending on the task in hand, such as for example slice displays in different planes, modified 3D displays or even calculated projections.

In addition to the method described above with its different embodiments, the inventors also propose at least one embodiment of a CT system having a dedicated control and computation unit and a number of workstations in different medical specialist areas connected thereto in the manner of a network to form a diagnosis system, with computer programs for performing the method steps of one of at least one embodiment of the preceding method being stored in the control and computation unit and the workstations.

Figure 1:
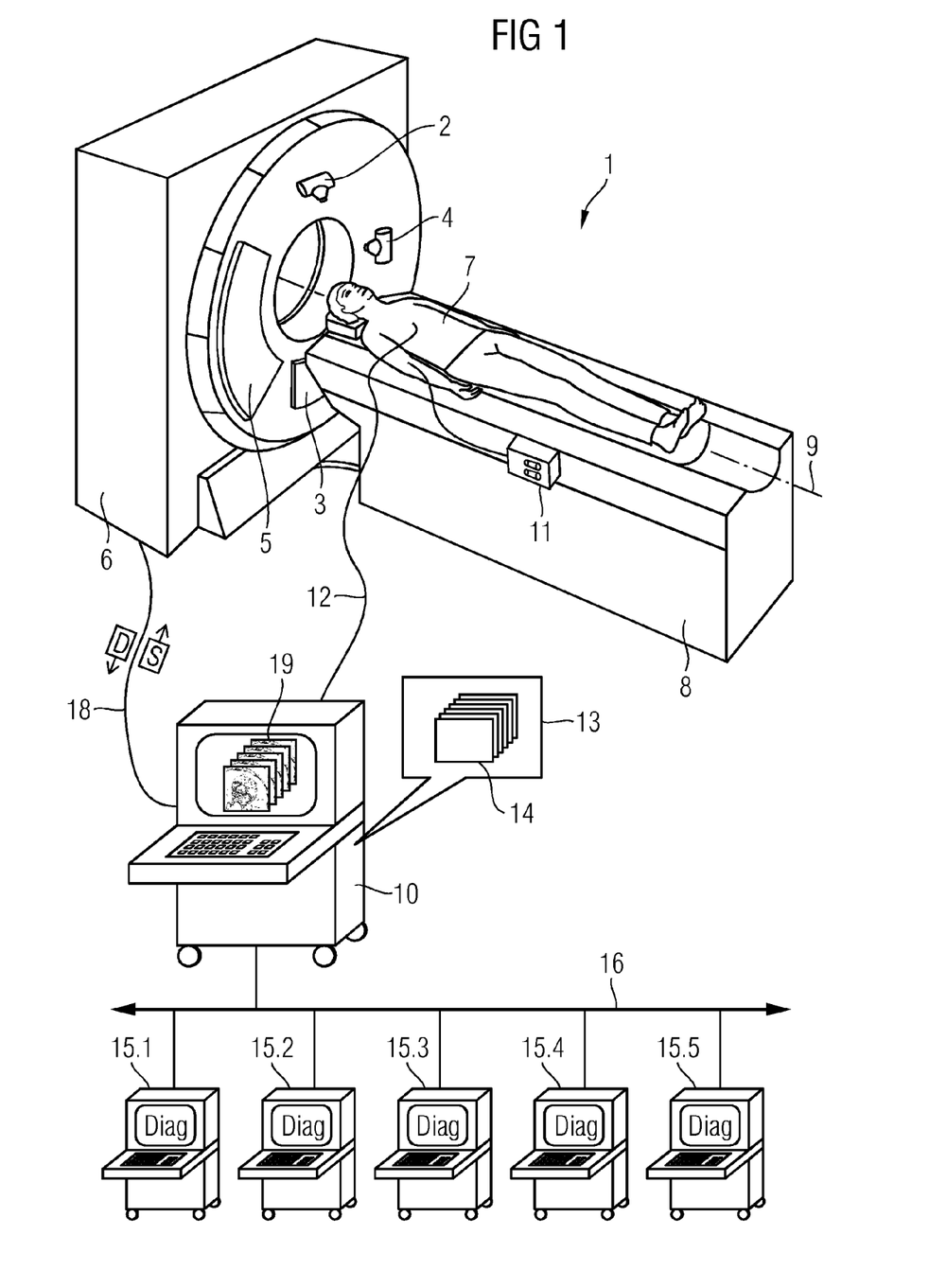
FIG. 1 shows a CT system with computer program for performing an embodiment of the inventive method.

FIG. 1 shows by way of example a CT system 1 with which the inventive method is performed. The CT system 1 shown has a first emitter/detector system with an x-ray tube 2 and a detector 3 located opposite it. Such a CT system 1 can optionally also have a second x-ray tube 4 with a detector 5 located opposite it. Both emitter/detector systems are present on a gantry, which is disposed in a gantry housing 6 and rotates during scanning about a system axis 9. If two emitter/detector systems are used, it is possible in a simple manner on the one hand to achieve increased temporal resolution for supplementary cardio examinations or it is possible to scan with different energies at the same time, so that material breakdown is also possible and as a result supplementary examination information can be supplied in the body regions under consideration.

The—generally polytraumatized—patient 7 is positioned on a movable examination couch 8, which can be moved along the system axis 9 through the scan field present in the gantry housing 6, in which process the attenuation of the x-ray radiation emitted by the x-ray tubes is measured by the detectors, with a whole-body topogram being recorded first, a z-distribution to different body regions taking place automatically and in some instances with manual assistance and the respectively reconstructed CT image data then only being distributed individually by way of a network 16 to the specialist diagnostic workstations 15.x in each instance for the respective diagnosis of relevance for the body regions.

In principle according to an embodiment of the invention a simple whole-body CT is performed but in addition a contrast agent bolus can be injected into the patient 7 with the aid of a contrast agent applicator 11, so that blood vessels can be identified more easily. For cardio recordings heart activity can also be measured with the aid of an EKG line 12 and an EKG-gated scan can be performed.

The CT system is controlled with the aid of a control and computation unit 10 by way of a control and data line 18, by way of which the raw data D from the detectors 3 and 5 and the control commands S are transferred. Present in the memory 13 of the control and computation unit 10 are computer programs 14, which can also perform an embodiment of the inventive method described above. CT image data 19, in particular also of the topogram, can additionally be output by way of this control and computation unit 10, it being possible to assist the distribution of the body regions by way of manual inputs.

Figure 2:
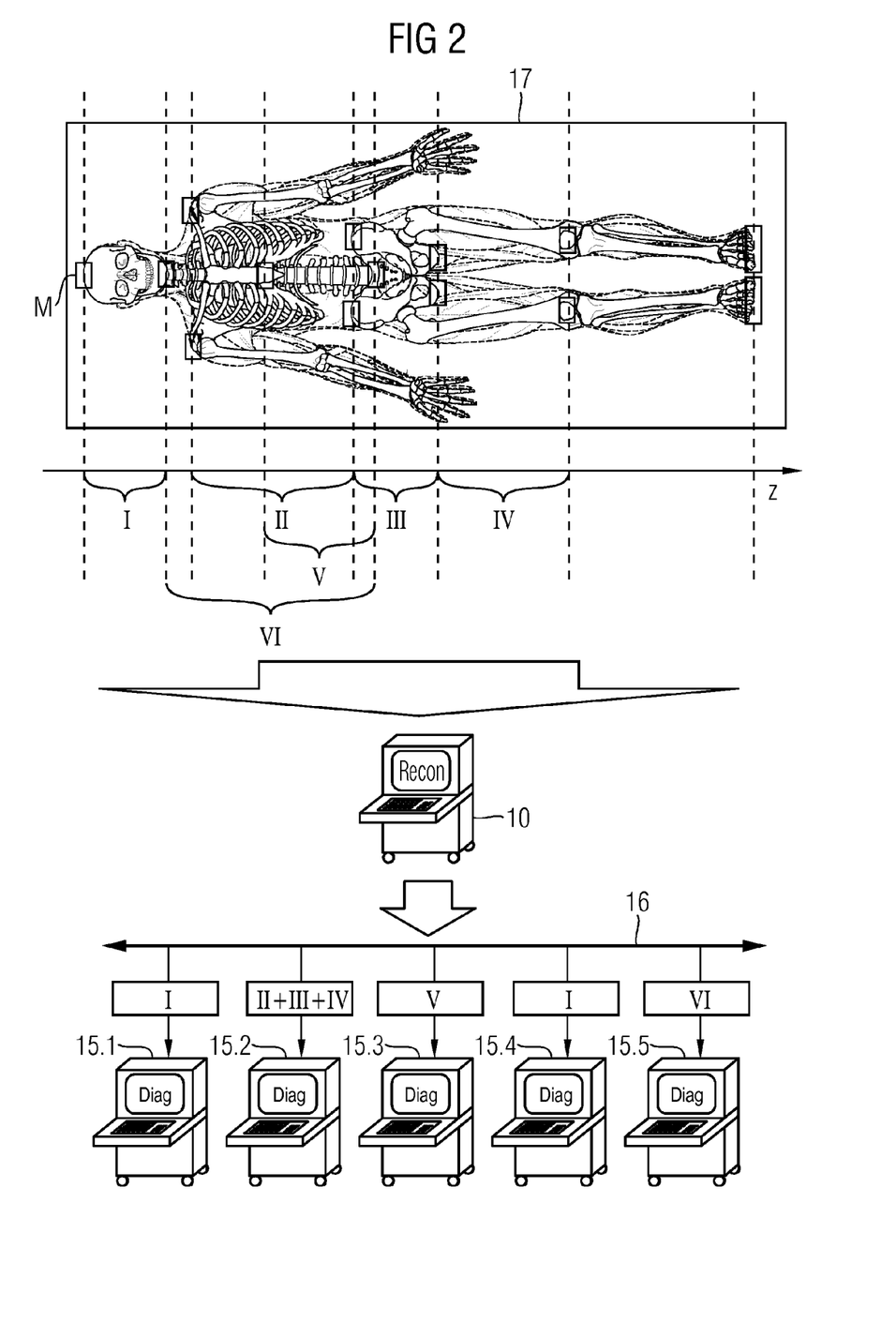
FIG. 2 shows a schematic diagram of a topogram with body marks and z-distribution to body regions, including common reconstruction and body region-specific distribution of the CT datasets to connected specialist diagnostic workstations.

FIG. 2 shows a schematic diagram of a topogram with body marks and z-distribution to body regions, including common reconstruction and body region-specific distribution of the CT datasets to connected specialist diagnostic workstations, in the form of a first scenario. According to this typical body structures, known as landmarks, are searched for in the topogram 17, which was recorded using the CT system from FIG. 1. In the topogram shown here these landmarks M are shown by rectangles. The landmarks M found in this manner are used to divide the topogram 17 into a plurality of body regions I-VI. After reconstruction of the detector data by means of the whole-body scan performed thereafter, the reconstructed CT image data is divided up according to the z-coordinates of the body regions found and specifically only the CT data required for the respective specific diagnosis—in other words fractionated whole-body CT image data—is sent by way of the network 16 to the specific diagnostic workstations 15.1 to 15.5.

In this instance identification of the body regions takes place for example by body parsing on topograms, so that the raw data does not have to be analyzed further and is already present for the individual body regions after the reconstruction. For the purpose of viewing the data special trauma layouts can be provided in the postprocessing applications, in which important views of the body regions are preconfigured, e.g. projection of the pelvic bone, in order to identify breaks, which can also be produced on the basis of identified landmarks.

Figure 3:
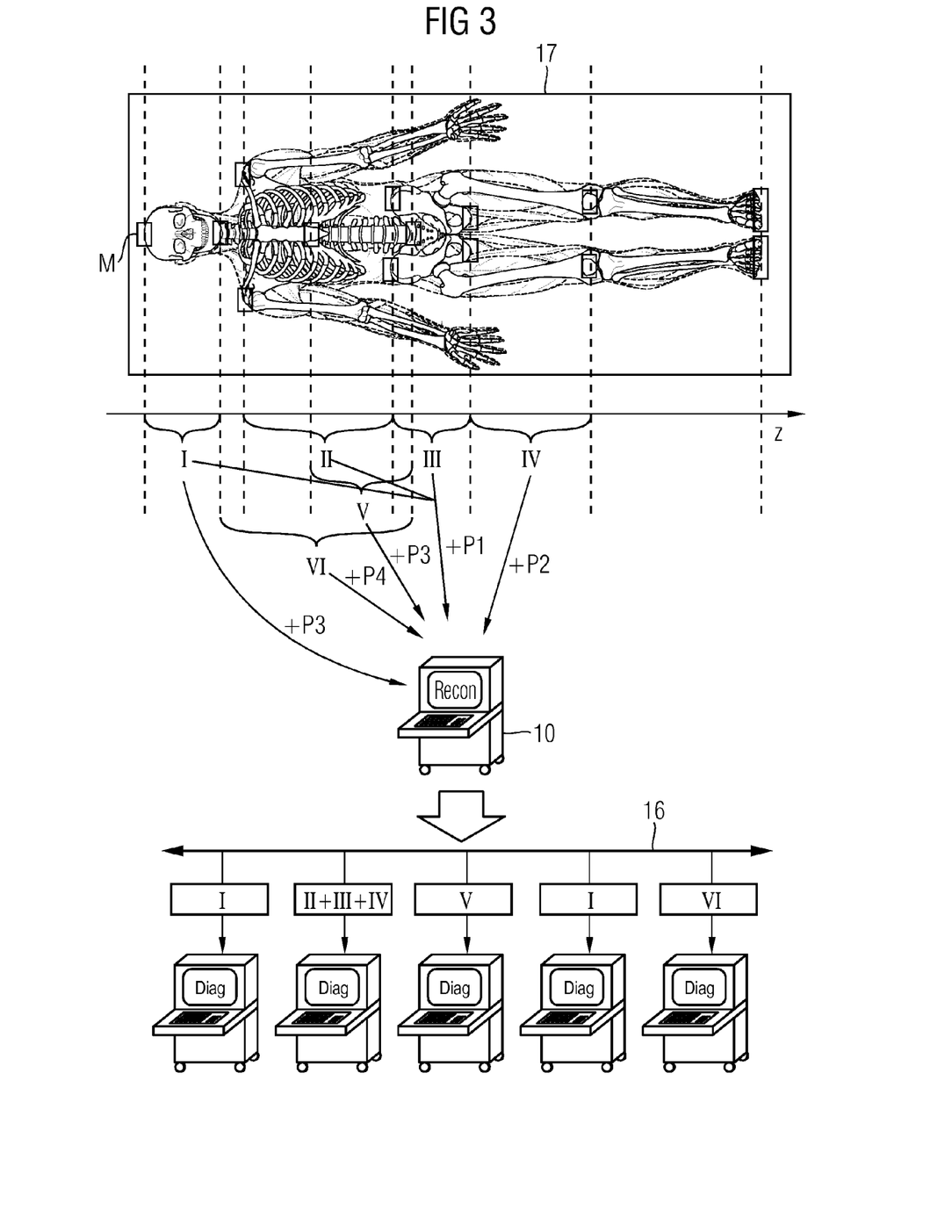
FIG. 3 shows a schematic diagram of a topogram with body marks and z-distribution to body regions, including individual reconstruction of the body regions with specific reconstruction parameters and body region-specific distribution of the CT datasets to connected specialist diagnostic workstations.

One improvement to this method can reside—as shown in FIG. 3—in the performance of an individual reconstruction of the individual body regions with individual reconstruction parameter sets P1-P4 in each instance in addition to the method shown in FIG. 2. In the example shown the body regions I, II and III are reconstructed with the parameter set P1, the body regions IV with the parameter set P2, the body regions I and V with the parameter set P3 and the body region VI with the parameter set P4, so that the best display conditions for the different diagnostic requirements, such as optimum bone display or optimum soft part display, are already present during reconstruction as the optimum parameter set has been selected.

Figure 4:
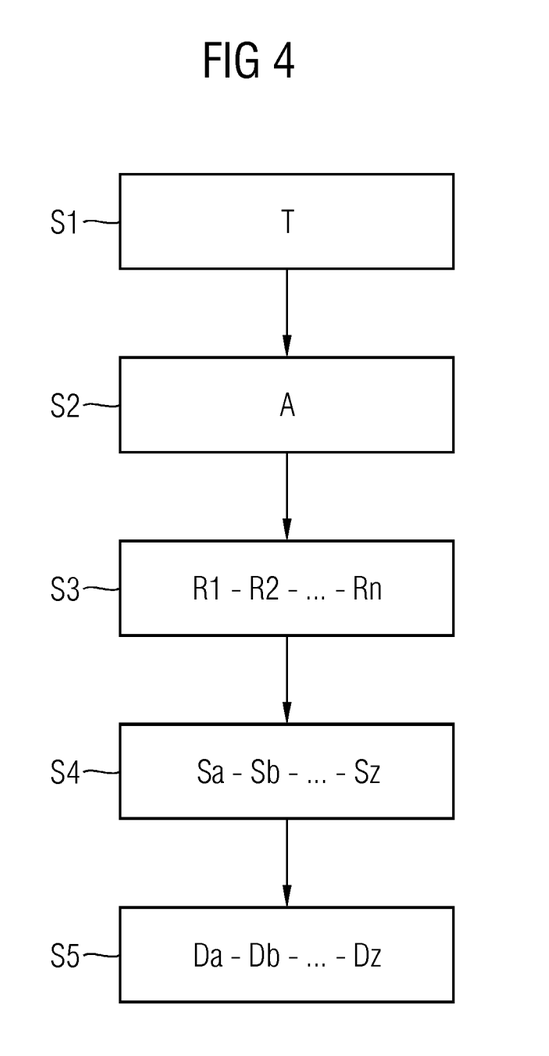
FIG. 4 shows a schematic diagram of the inventive method for recording and distributing whole-body CT data of a polytraumatized patient using a CT system.

Finally FIG. 4 also shows a schematic diagram of an embodiment of the inventive method for recording and distributing whole-body CT data of a polytraumatized patient using a CT system. According to this in method step S1 a whole-body topogram "T" is first produces with the aid of a CT system and then in method step S2 there is a division and assignment "A" of z-coordinate regions of the whole-body topogram to different body regions. This is followed in method step S3 by the actual whole-body CT scan in which CT raw data is recorded, which is reconstructed after being assigned to the different body regions on the basis of the determined z-coordinate regions in a common manner or using different reconstruction parameter sets for the body region-specific reconstruction datasets "R1 to Rn". In method step S4 diagnosis-specific image datasets "Sa to Sb" are then produced, from which all unnecessary data is eliminated before they are transferred to the individual specialist diagnostic workstations. Finally in method step S5 the actual body region-specific differential diagnosis "Da to Dz" takes place at the individual diagnostic workstations.

Generally therefore an embodiment of the invention presents a method and CT system for recording and distributing whole-body CT data of a polytraumatized patient, with a whole-body topogram being produced first with division and allocation of z-coordinate regions of the whole-body topogram to different body regions, a whole-body CT scan being performed with the recording of CT raw data, the CT raw data being assigned to the different body regions and CT image datasets being reconstructed on a computer of the CT system and then only body region-specific CT image datasets being sent to a number of remote diagnostic workstations operated by technical specialists.

Even though the invention was illustrated and described in detail using the example embodiment, the invention is not restricted by the disclosed examples and other variations can be derived therefrom by the person skilled in the art without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for recording and distributing whole-body CT data of a polytraumatized patient using a CT system, the method comprising:
   producing a whole-body topogram including division and assignment of z-coordinate regions of the whole-body topogram to different body regions;
   performing a whole-body CT scan with the recording of CT raw data;
   assigning all of the CT raw data to the different body regions based on the determined z-coordinate regions;
   reconstructing CT image datasets of the CT system, the CT image datasets representing the different body regions of the z-coordinate regions; and
   sending each body region-specific CT image dataset to a remote workstation operated by a technical specialist based on the body region represented by the body region-specific CT image dataset to determine a diagnosis in respect of the respective different body regions sent thereto.

2. The method of claim 1, wherein each body region-specific CT image dataset is reconstructed using individual reconstruction parameters.

3. The method of claim 1, wherein the body regions in the topogram are generated by way of automatic identification methods for typical body marks.

4. The method of claim 3, wherein the body regions are configured to overlap at least partially.

5. The method of claim 3, wherein manual correction of the previously automatically identified body regions is permitted.

6. The method of claim 1, wherein the different transferred CT datasets of the body regions are shown at the different workstations in different display modes tailored to the respective diagnosis.

7. A CT system comprising:
a dedicated control and computation unit; and
a number of workstations in different medical specialist areas connected to the dedicated control and computation unit in a network to form a diagnosis system, at least one of the dedicated control and computation unit and the workstations including computer programs that, when executed, cause the at least one of the dedicated control and computation unit and the workstations to:
produce a whole-body topogram including division and assignment of z-coordinate regions of the whole-body topogram to different body regions;
perform a whole-body CT scan with the recording of CT raw data;
assign all of the CT raw data to the different body regions based on the determined z-coordinate regions;
reconstruct CT image datasets of the CT system, the CT image datasets representing the different body regions of the z-coordinate regions; and
send each body region-specific CT image dataset to a remote workstation operated by a technical specialist based on the body region represented by the body region-specific CT image dataset to determine a diagnosis in respect of the respective different body regions sent thereto.

8. The method of claim 2, wherein the body regions in the topogram are generated by way of automatic identification methods for typical body marks.

9. The method of claim 2, wherein the body regions are configured to overlap at least partially.

10. The CT system of claim 7, wherein the body regions in the topogram are generated by way of automatic identification methods for typical body marks.

11. The method of claim 4, wherein manual correction of the previously automatically identified body regions is permitted.

12. A non-transitory computer readable medium including program segments that, when executed on a computer device, cause the computer device to implement the method of claim 1.

13. The CT system claim 10, wherein manual correction of the previously automatically identified body regions is permitted.

14. The CT system of claim 7, wherein the body regions are configured to overlap at least partially.

15. The non-transitory computer readable medium of claim 12, wherein the body regions in the topogram are generated by way of automatic identification methods for typical body marks.

16. The non-transitory computer readable medium of claim 15, wherein manual correction of the previously automatically identified body regions is permitted.

17. The non-transitory computer readable medium of claim 12, wherein the body regions are configured to overlap at least partially.

* * * * *